US005607848A

United States Patent [19]

Katsumata et al.

[11] Patent Number: 5,607,848
[45] Date of Patent: Mar. 4, 1997

[54] PROCESS FOR PRODUCING OPTICALLY ACTIVE 4-HYDROXY-2-KETOGLUTARIC ACID USING MICROORGANISMS

[75] Inventors: Ryoichi Katsumata; Shinichi Hashimoto, both of Machida; Keiko Ochiai, Ebina, all of Japan

[73] Assignee: Kyowa Hakko Kogyo Co., Ltd., Japan

[21] Appl. No.: 395,707

[22] Filed: Feb. 28, 1995

[30] Foreign Application Priority Data

Mar. 1, 1994 [JP] Japan ................................. 6-31335
Apr. 21, 1994 [JP] Japan ................................. 6-83065

[51] Int. Cl.$^6$ ....................................................... C12P 7/50
[52] U.S. Cl. ........................ 435/143; 435/822; 435/874; 435/877
[58] Field of Search ................................. 435/143, 822, 435/874, 877

[56] References Cited

U.S. PATENT DOCUMENTS 5,374,542 12/1994 Katsumata et al. ...................... 435/107

FOREIGN PATENT DOCUMENTS 3-266995 11/1991 Japan .
636262 12/1978 U.S.S.R. .

OTHER PUBLICATIONS

Maruyama K, J. Biochem 108:327–333 (1990).
ATCC Catalogue of Bacteria and Bacteriophages pp. v and 78 (1992).
"Metabolism of γ-Hydroxyglutamic Acid", A. Goldstone et al., The Journal of Biological Chemistry, 237(11):3476–3485 (1962).
"Enzymatic Steps in the Conversion of γ-Hydroxyglutamate to Glyoxylate and Alanine", U. Maitra et al., The Journal of Biological Chemistry, 238 (11):3660–3669 (1963).
"DL-2-Keto-4-hydroxyglutarate", E. E. Dekker et al., Methods in Enzymology, vol. XLI, pp. 115–118 (1975).

Primary Examiner—Irene Marx
Assistant Examiner—S. Saucier
Attorney, Agent, or Firm—Finnegan, Henderson, Farabow, Garrett & Dunner, L.L.P.

[57] ABSTRACT

The present invention provides a process for producing an optically active 4-hydroxy-2-ketoglutaric acid, by mixing glyoxylic acid, pyruvic acid and a microorganism to form the optically active 4-hydroxy-2-ketoglutaric acid in an aqueous medium.

2 Claims, No Drawings

PROCESS FOR PRODUCING OPTICALLY ACTIVE 4-HYDROXY-2-KETOGLUTARIC ACID USING MICROORGANISMS

BACKGROUND OF THE INVENTION

1. Field of the Invention

The present invention relates to a process for producing an optically active 4-hydroxy-2-ketoglutaric acid in which a biocatalyst having an activity for formation of the optically active 4-hydroxy-2-ketoglutaric acid from pyruvic acid and glyoxylic acid is used to produce the optically active 4-hydroxy-2-ketoglutaric acid from pyruvic acid or a compound capable of being converted into pyruvic acid, and glyoxylic acid. The optically active 4-hydroxy-2-ketoglutaric acid is useful as a starting material for synthesizing a medicament.

2. Description of the Prior Art

As conventional methods for producing the optically active 4-hydroxy-2-ketoglutaric acid, chemical deamination of threo- and erythro-4-hydroxy-L-glutamic acid to obtain L- and D-4-hydroxy-2-ketoglutaric acid, respectively (J. Biol. Chem., 288, 3660 (1963)) and resolution of DL-4-hydroxy-2-ketoglutaric acid synthesized from oxaloacetic acid and glyoxylic acid into D- and L-form (Methods in Enzymology, 17 part B, 253) are known. It is also possible to enzymatically synthesize 4-hydroxy-2-ketoglutaric acid from pyruvic acid and glyoxylic acid by using ketohydroxyglutaric acid aldolase present in animals and *E. coli*. However, the 4-hydroxy-2-ketoglutaric acids obtained by these methods are known to be only mixtures of D- and L-forms (Methods in Enzymology, 41 part B, 115).

These conventional methods are insufficient for the industrial application due to the following points: (1) the starting materials are expensive; (2) resolution step of DL-form is required; (3) yield is low, etc. Consequently, there exists a need for development of a method for producing the optically active 4-hydroxy-2-ketoglutaric acid which is industrially applicable and advantageous.

OBJECTS AND SUMMARY OF THE INVENTION

An object of the present invention is therefore to provide a process for producing the optically active 4-hydroxy-2-ketoglutaric acid which is industrially applicable and advantageous.

Means Taken for Solving the Problem

According to the present invention, there is provided a process for producing an optically active 4-hydroxy-2-ketoglutaric acid, which comprises allowing glyoxylic acid and pyruvic acid to coexist with a biocatalyst which has an activity of forming the optically active 4-hydroxy-2-ketoglutaric acid from pyruvic acid and glyoxylic acid in an aqueous medium to convert glyoxylic acid into the optically active 4-hydroxy-2-ketoglutaric acid, and recovering the optically active 4-hydroxy-2-ketoglutaric acid from the aqueous medium.

As used herein, the term "optically active 4-hydroxy-2-ketoglutaric acid" refers to D-4-hydroxy-2-ketoglutaric acid [(R)-4-hydroxy-2-ketoglutaric acid] or L-4-hydroxy-2-ketoglutaric acid [(S)-4-hydroxy-2-ketoglutaric acid].

More specifically, the present invention provides a process for producing D- or L-4-hydroxy-2-ketoglutaric acid, which comprises allowing glyoxylic acid and pyruvic acid to coexist with a biocatalyst which has an activity of forming D- or L-4-hydroxy-2-ketoglutaric acid from pyruvic acid and glyoxylic acid in an aqueous medium to convert glyoxylic acid into D- or L-4-hydroxy-2-ketoglutaric acid, and recovering D- or L-4-hydroxy-2-ketoglutaric acid from the aqueous medium.

DETAILED DESCRIPTION OF THE INVENTION

The present invention will be described in detail below.

The biocatalysts used in the present invention may include cells, a culture, and processed cells of a microorganism.

The "processed cells of microorganism" include treated cells such as dried cells, lyophilized cells, surfactant-treated cells, enzymatically treated cells, ultrasonically treated cells, mechanically ground cells and solvent-treated cells; protein-containing fractions of the cells; immobilized products of processed or processed cells; and the like.

Any microorganism which has the ability to form the optically active 4-hydroxy-2-ketoglutaric acid from pyruvic acid and glyoxylic acid can be employed. Examples of the microorganisms having such activity are those belonging to the genus Cellvibrio, Bacillus, Pseudomonas, Paracoccus, Providencia, Rhizobium or Morganella.

When D-4-hydroxy-2-ketoglutaric acid is prepared, microorganisms which belong to the genus Cellvibrio or Bacillus and have the ability to form D-4-hydroxy-2-ketoglutaric acid from pyruvic acid and glyoxylic acid are used.

Specifically, the microorganisms may include *Cellvibrio gilvus* ATCC 13127 strain, Bacillus sp. OC187 strain, Bacillus sp. S16 strain, etc. ATCC 13127 and OC187 strains can be deprived of their activities of formation of L-4-hydroxy-2-ketoglutaric acid by heat-treating them at a temperature of 60° to 90° C. for a period of time of 5 minutes to 2 hours. Alternatively, such inactivated strains can be obtained by mutagenizing microorganisms, which belong to the genus Cellvibrio or Bacillus and has the ability to form D-4-hydroxy-2-ketoglutaric acid from pyruvic acid and glyoxylic acid, by a conventional mutagenesis technique, for example, with N-methyl-N'-nitro-N-nitrosoguanidine (NTG), and then screening the resulting mutants for the inactivation in the formation of L-4-hydroxy-2-ketoglutaric acid. S16 strain is a mutant derived from OC187 and which lacks the activity for formation of L-4-hydroxy-2-ketoglutaric acid.

Bacillus sp. OC187 strain has been isolated by the present inventors from soil in Machida city, Tokyo, Japan. The bacteriological properties of the strain OC187 are shown in Tables 1-1 to 1-6 below.

(A) Morphological properties

TABLE 1-1

| Morphological properties | |
|---|---|
| Cell morphology: | rod |
| Cell size: | 0.8–1.0 × 3.0–4.0 μm |
| Cell polymorphism: | not observed |
| Cell motility: | observed |
| Position of flagella: | peripheral |
| Spore: | observed |
| Spore morphology: | ellipse |
| Position of spore: | central |

(B) Cultural Characteristics in Various Media

TABLE 1-2

Cultural Characteristics in Various Media

| Bouillon-Agar Medium (Meat extract) | growth: | Abundant |
|---|---|---|
| | surface: | smooth |
| | color: | light pink |
| | gloss: | none |
| | diffusible pigments: | negative |
| Bouillon-liquid medium (Meat extract) | surface growth: | not observed |
| | turbidity: | positive |
| Bouillon-Gelatin medium Liquefaction of gelatin | | negative |
| Litmus milk | reaction: | acid |
| | coagulation: | positive |
| | liquefaction: | negative |

(C) Physiological Properties

TABLE 1-3

Physiological Properties-1

| ① Gram staining: | + or − |
|---|---|
| ② Reduction to nitrate salt: | − |
| ③ Denitrification reaction: | + |
| ④ Methyl red test: | − |
| ⑤ VP test: | + |
| ⑥ Indole production: | − |
| ⑦ Hydrogen sulfide production: | − |
| ⑧ Utilization of citric acid | |
| Koser's method: | + |
| Christensen's method: | + |
| ⑩ Utilization of inorganic nitrogen | |
| Nitrates: | + |
| Ammonium salts: | + |
| ⑪ Pigment production | |
| King A medium: | − |
| King B medium: | − |
| ⑫ Urease: | + |
| ⑬ Oxidase: | − |
| ⑭ Catalase: | + |
| ⑮ Growth range: | |
| pH; | 5.2–9.7 |
| Optimum pH; | about 7.0 |
| Temperature; | 15–56° C. |
| Optimum temp.; | around 47° C. |
| ⑯ Attitude toward oxygen | |
| Aerobic | + |
| Anaerobic | + |
| (facultative anaerobic) | |
| ⑰ OF test | fermentative |

+: Positive, −: Negative

TABLE 1-4

| Acid and Gas Production (6th day) | Physiological Properties-2 | | | |
|---|---|---|---|---|
| | Conditions | | | |
| | Aerobic | | Anaerobic | |
| | Acid | Gas | Acid | Gas |
| 1. L-Arabinose: | + | − | + | − |
| 2. D-Xylose: | + | − | − | − |
| 3. D-Glucose: | + | − | + | − |
| 4. D-Mannose: | + | − | + | − |
| 5. D-Fructose: | + | − | + | − |

TABLE 1-4-continued

| Acid and Gas Production (6th day) | Physiological Properties-2 | | | |
|---|---|---|---|---|
| | Conditions | | | |
| | Aerobic | | Anaerobic | |
| | Acid | Gas | Acid | Gas |
| 6. D-Galactose: | + | − | − | − |
| 7. Maltose: | + | − | + | − |
| 8. Sucrose: | + | − | + | − |
| 9. Lactose: | − | − | − | − |
| 10. Trehalose: | + | − | + | − |
| 11. D-Sorbitol: | − | − | − | − |
| 12. D-Mannitol: | + | − | + | − |
| 13. Inositol: | − | − | − | − |
| 14. Glycerol: | + | − | − | − |
| 15. Starch: | + | − | + | − |

+: Positive, −: Negative (D) Other Properties

TABLE 1-5

| Other Properties | |
|---|---|
| 1. Degradation of esculin: | + |
| 2. Degradation of malonic acid: | − |
| 3. Degradation of arginine: | + |
| 4. Decarboxylation of lysine: | − |
| 5. Decarboxylation of ornithine: | − |
| 6. Deamination of phenylalanine: | − |
| 7. Resistance to sodium chloride: | viable at 10% |

+: Positive, −: Negative (E) Chemotaxonomic Properties

TABLE 1-6

| Chemotaxonomic Properties | |
|---|---|
| ① Base composition of DNA (G + C mol %): | 45.9 |
| ② Cellular lipid · major quinone: | MK-7 |
| ③ Diamino acid composition of cell wall peptidoglycan: | meso-$A_2$ pm |

The strain having the bacteriological properties mentioned above was classified according to Bergey's Manual of Systematic Bacteriology, Vol.2 (1986). As a result, the strain was classified to the genus Bacillus and was designated as the Bacillus sp. OC187.

Bacillus sp. OC187 and S16 strains were deposited with the National Institute of Bioscience and Human-Technology, Agency of Industrial Science and Technology in Japan on Feb. 24, 1994 as FERM BP-4646 and FERM BP-4647, respectively, under the Budapest Treaty.

For producing L-4-hydroxy-2-ketoglutaric acid, microorganisms of the genus Pseudomonas, Paracoccus, Providencia, Rhizobium or Morganella are preferably used. Specifically, those further having an ability to form L-4-hydroxy-2-ketoglutaric acid from pyruvic acid or a compound capable of being converted into pyruvic acid by the microorganisms and glyoxylic acid are used. Those which do not substantially produce D-4-hydroxy-2-ketoglutaric acid are more preferable.

Specific examples of the strains are *Pseudomonas putida* ATCC 795, *Pseudomonas putida* ATCC 4359, *Pseudomonas saccharophila* ATCC 9114 (=ATCC 15946; IAM Catalogue of Strains (1993)), *Pseudomonas boreopolis* ATCC 15452, *Pseudomonas taetrolens* ATCC 17466, *Pseudomonas oleovorans* ATCC 8062, *Paracoccus denitrificans* ATCC 19367,

*Providencia rustigianii* ATCC 13159, *Rhizobium meliloti* RCR 2001 (FERM BP-4582), and *Morganella morganii* ATCC 25830.

*Rhizobium meliloti* RCR 2001 strain was deposited with the National Institute of Bioscience and Human-Technology, Agency of Industrial Science and Technology in Japan on Feb. 24, 1994 as FERM BP-4582 under the Budapest Treaty.

Culturing of the microorganisms used in the present invention can be carried out by using a conventional synthetic or natural medium. When a bacterium of the genus Cellvibrio or Vibrio is used to synthesize D-4-hydroxy-2-ketoglutaric acid, D-galactonic acid is usable as a carbon source. When L-4-hydroxy-2-ketoglutaric acid is synthesized by using the other microorganisms, other carbon sources, such as saccharides, e.g., glucose, fructose, sucrose, maltose, molasses containing these compounds, starch and starch hydrolysates; organic acids, e.g., acetic acid, lactic acid, gluconic acid and propionic acid; alcohols, e.g., ethanol and propanol, and the like, are usable, so long as they can be assimilated by the microorganism used.

Various nitrogen-containing organic compounds are usable as nitrogen source, such as ammonia; ammonium salts, e.g., ammonium sulfate, ammonium chloride, ammonium acetate and, ammonium phosphte; urea; nitrate salts, as well as peptone, meat extract, yeast extract, corn steep liquor, and the like, so long as they can be assimilated by the microorganism used.

Potassium dihydrogen phosphate, potassium hydrogen phosphate, ammonium sulfate, ammonium chloride, sodium chloride, magnesium sulfate, ferrous sulfate, manganese sulfate and the like can be used as inorganic salts, so long as they are can be assimilated by the microorganism used. In addition to these salts, trace elements such as calcium, zinc, boron, copper, cobalt, molybdenum, and the like may be added to the culture medium.

If necessary, the culture medium may contain a vitamin such as thiamin and biotin, an amino acid such as glutamic acid and aspartic acid, and/or a nucleic acid-related compound such as adenine and guanine.

The optically active 4-hydroxy-2-ketoglutaric acid can be synthesized from pyruvic acid or a compound capable of being converted into pyruvic acid and glyoxylic acid, by using either a method wherein the substrates are added to the culture in which the microorganism is growing or a method wherein the substrates are applied to the culture in which growth of the microorganism has been completed, to the cells isolated from the culture, or to the processed cells of microorganism.

When the former method is employed, pyruvic acid and glyoxylic acid can each be added to the culture medium either at the starting point of or in the course of the microorganism growth in a concentration range of 1 to 200 g/l, preferably 20 to 200 g/l. The period of time required for the culture will vary depending upon the microorganism used. However, it takes about 10 to 100 hours.

When the latter method is employed, it can be carried out by reacting 1 to 200 g/l, preferably 20 to 200 g/l of pyruvic acid, with 1 to 200 g/l, preferably 20 to 200 g/l of glyoxylic acid, in the presence of 0.1 to 200 g/l, preferably 5 to 100 g/l of cells of the microorganism or processed product thereof (in the latter case, calculated in amount prior to treatment) in an aqueous medium at a pH value of 3 to 11, preferably 5 to 9, at a temperature of 15° to 60 ° C., preferably 25° to 45° C. The reaction time is about 30 minutes to about 80 hours.

Examples of the aqueous medium usable in the present invention include, for example, phosphate buffer and saline.

If necessary, a surfactant such as Triton X-100 (Nacalai Tesque, Inc.) and Nymeen (Nippon oil & fats CO., LTD.) and an organic solvent such as toluene and xylene may also be added in the aqueous medium in an amount of 0.1 to 20 g/l.

Any compound capable of being converted into pyruvic acid by the biocatalyst which has an activity of forming the optically active 4-hydroxy-2-ketoglutaric acid from pyruvic acid and glyoxylic acid, can be used instead of pyruvic acid. Examples of the compounds are saccharides such as glucose, fructose and maltose; glycerol; lactic acid, ammonium lactate and the like.

Isolation of the optically active 4-hydroxy-2-ketoglutaric acid can be carried out by the conventional method used for isolation of an organic acid from an aqueous medium. For example, the reaction supernatant may be separated from the cells or processed product thereof by centrifugation and applied to either or both of an ion exchange resin and a membrane.

The optically active 4-hydroxy-2-ketoglutaric acid obtainable by the present invention is useful as a material for synthesizing a medicament. For example, starting from 4-hydroxy-2-ketoglutaric acid, carbapenem antibiotics can be synthesized via 4-hydroxyproline. Conversion of 4-hydroxy-2-ketoglutaric acid into 4-hydroxyproline can be carried out according to the method described in Japanese Unexamined Patent Publication No. 266995/91. The carbapenem antibiotics can be obtained by synthesizing N-p-nitrobenzyloxycarbonyl-3-mercapto-pyrrolidine from 4-hydroxyproline according to the method described in Heterocycles, 24, 1331 (1986) and then treating the intermediate according to the method described in Japanese Unexamined Patent Publication No. 32879/83.

By the present invention, the optically active 4-hydroxy-2-ketoglutaric acid which is useful as a material for synthesizing a medicament can advantageously be obtained on industrial scale.

DESCRIPTION OF THE PREFERRED EMBODIMENTS

The present invention is described in more detail by the following examples. However, the Examples are not intended to restrict the scope of the present invention.

EXAMPLE 1

*Cellvibrio gilvus* ATCC 13127 strain was inoculated into 3 ml of L medium (containing 10 g of Bactopeptone, 5 g of yeast extract and 10 g of NaCl in 1 liter of water and being adjusted to pH 7.0), and then cultured for 16 hours at 30° C. with shaking. Then, 2 ml of the culture was then inoculated into 20 ml of GNMS medium having the composition shown in Table 2 below.

TABLE 2

| Composition of GNMS medium (amounts per liter) | |
|---|---|
| Calcium D-galactonate | 10 g |
| $KH_2PO_4$ | 2 g |
| $(NH_4)_2SO_4$ | 2 g |
| $FeSO_4 \cdot 7H_2O$ | 5 mg |
| $MnSO_4 \cdot 7H_2O$ | 2 mg |
| $CaCl_2$ | 10 mg |
| Yeast extract | 1 g |
| Peptone | 1 g |
| pH | 7.0 |

Two 10 ml aliquots of this medium were put into two test tubes separately, and cultured for 20 hours. After cultivation, one test tube of the two was subjected to heat treatment at 80° C. for 1 hour and the other was maintained at 30° C. In each case, the cells were collected by centrifugation, and resuspended in 1 ml of sterilized reactant solution (a) (containing 3 g of $KH_2PO_4$, 6 g of $NaH_2PO_4$, 1 g of $NH_4$ Cl, 0.16 g of $MgSO_4 \cdot 7H_2O$, 5 g of NaCl, 11 mg of $CaCl_2$ 100 mmol sodium pyruvate and 100 mmol glyoxylic acid in 1 liter of purified water and being adjusted to pH 7.0 with NaOH), and the suspension was shaken in a 2059 tube (Falcon Co.) at 37° C. for 5 hours. After the completion of reaction, the cells were removed from the suspension by centrifugation, and the amount of 4-hydroxy-2-ketoglutaric acid formed in the supernatant was determined by HPLC using SUMICHIRAL OA-5000 column (Sumitomo Chemical Co.). The results are shown in Table 3. In this determination, standard compounds for D- and L-4-hydroxy-2-ketoglutaric acid were prepared according to the methods described in J. Biol. Chem., 237, 476 (1962) and J. Biol. Chem., 238, 3660 (1963), respectively.

TABLE 3

| Heat treatment | Yield of 4-hydroxy-2-ketoglutaric acid (mM) | |
| --- | --- | --- |
|  | D-form | L-form |
| not done | 32.0 | 8.0 |
| done | 30.0 | 0.0 |

EXAMPLE 2

Three ml portions of L medium were put into test tubes. After sterilization, each of the microorganisms shown in Table 5 was inoculated thereinto and cultured for 16 hours at 30° C. with shaking. Then 1 ml of each culture was inoculated into 10 ml of GMS medium having the composition shown in Table 4 below in a test tube and cultured for 20 hours.

TABLE 4

| Composition of GMS medium (amounts per liter) | |
| --- | --- |
| Glucose | 20 g |
| $KH_2PO_4$ | 2 g |
| $(NH_4)_2SO_4$ | 2 g |
| $FeSO_4 \cdot 7H_2O$ | 5 mg |
| $MnSO_4 \cdot 7H_2O$ | 2 mg |
| $MgSO_4 \cdot 7H_2O$ | 0.5 g |
| $CaCl_2$ | 10 mg |
| Yeast extract | 1 g |
| Peptone | 1 g |
| pH | 7.0 |

After cultivation, in each case, the cells were collected by centrifugation, and suspended in 1 ml of sterilized reactant solution (b) (containing 3 g of $KH_2 PO_4$, 6 g of $NaH_2 PO_4$, 1 g of $NH_2$ Cl, 0.16 g of $MgSO_4 \cdot 7H_2O$, 5 g of NaCl, 11 mg of $CaCl_2$, 100 mmol sodium pyruvate, 100 mmol glyoxylic acid and 10 mmol arsenous acid in 1 liter of purified water and being adjusted to pH 7.0 with NaOH), and the suspension was shaken in a 2059 tube (Falcon Co. ) at 30° C. for 5 hours. After the completion of reaction, the cells were removed from the suspension separately by centrifugation, and the amount of 4-hydroxy-2-ketoglutaric acid formed in the supernatant was determined by HPLC using SUMICHIRAL OA-5000 column (Sumitomo Chemical Co.). The results are shown in Table 5.

TABLE 5

| Strains | Yield of 4-hydroxy-2-ketoglutaric acid (mM) | |
| --- | --- | --- |
|  | D-form | L-form |
| Pseudomonas putida ATCC 795 | 0.0 | 61.3 |
| Pseudomonas putida ATCC 4359 | 0.0 | 29.8 |
| Pseudomonas saccharophila ATCC 9114 (= ATCC 15946) | 0.0 | 40.5 |
| Pseudomonas boreopolis ATCC 15452 | 0.0 | 14.9 |
| Pseudomonas taetrolens ATCC 17466 | 0.0 | 35.0 |
| Pseudomonas oleovorans ATCC 8062 | 0.0 | 33.0 |
| Paracoccus denitrificans ATCC 19367 | 0.0 | 40.0 |
| Providencia rustigianii ATCC 13159 | 0.0 | 40.0 |
| Rhizobium meliloti RCR 2001 | 0.0 | 15.7 |
| Morganella morganii ATCC 25830 | 0.0 | 10.0 |

EXAMPLE 3

The same solutions as the reactant solution (a) in Example 1 were prepared except that 20 g of glucose, 20 g of glycerol or 20 g of ammonium lactate was used instead of 100 mmol sodium pyruvate. In these reactant solutions were suspended, cells obtained by culturing Pseudomonas putida ATCC 795 strain as described in Example 2, and the suspensions were shaken at 30 ° C. for 5 hours as described in Example 2. After the completion of reactions, in each case, the cells were removed from the suspension by centrifugation, and the amount of 4-hydroxy-2-ketoglutaric acid formed in the supernatant was determined by HPLC using SUMICHIRAL OA-5000 column (Sumitomo Chemical Co.). The results are shown in Table 6.

TABLE 6

| Reaction substrates | Yield of 4-hydroxy-2-ketoglutaric acid (mM) |
| --- | --- |
| glucose | 15.0 |
| glycerol | 10.0 |
| ammonium lactate | 6.7 |

EXAMPLE 4

Cellvibrio gilvus ATCC 13127 strain was inoculated into 9 ml of L medium and cultured for 16 hours at 30 ° C. with shaking. Whole amount of this culture was then inoculated into 300 ml of GNMS medium in 2 liter volume Erlenmeyer flask and cultured for 20 hours at 30° C. with shaking. After heat treatment of this culture for 1 hour at 80 ° C., the cells were collected by centrifugation, and suspended in 60 ml of the reactant solution (a) in 300 ml volume beaker, and the suspension was stirred while maintaining pH at 6.5 with 1N sulfuric acid. After 6 hours, 3 ml of 2M sodium pyruvate and 3 ml of 2M sodium glyoxylate were added. After 24 hours from the starting point of this reaction, the cells were removed from the suspension by centrifugation, and the amount of 4-hydroxy-2-ketoglutaric acid formed in the supernatant was determined by HPLC. The amount of D-4-hydroxy-2-ketoglutaric acid was determined to be 125 mM and L- form was not detected.

The above supernatant (50 ml) was passed through a column filled with Diaion PA 416 (Mitsubishi Kasei, Corp.), followed by elution by an exponential gradient of 0–6M formic acid. Fractions containing 4-hydroxy-2-ketoglutaric acid which was eluted with 6–8 column volumes eluent were combined and concentrated under reduced pressure. Afterward, the concentrate was provided with 0.01M $Ca(OH)_2$ and adjusted to pH 7.5 therewith. Acetone was added to the resulting solution to precipitate calcium salt of D-4-hydroxy-2-ketoglutaric acid. Thus, 0.5 g of calcium salt of D-4-hydroxy-2-ketoglutaric acid was obtained.

EXAMPLE 5

*Pseudomonas putida* ATCC 795 strain was inoculated into 9 ml of L medium and cultured for 16 hours at 30° C. with shaking. Whole amount of this culture was then inoculated into 300 ml of GMS medium in 2 liter volume Erlenmeyer flask and cultured for 20 hours at 30° C. with shaking. The resulting culture was centrifuged, the collected cells were resuspended in 60 ml of the reactant solution (b), and the suspension was stirred in 300-ml beaker while maintaining pH at 6.5 with 1N sulfuric acid. After 6 hours, 3 ml of 2M sodium pyruvate and 3 ml of 2M sodium glyoxylate were added. After 24 hours from the starting point of this reaction, the cells were removed from the suspension by centrifugation, and the amount of 4-hydroxy-2-ketoglutaric acid formed in the supernatant was determined by HPLC. The amount of L-4-hydroxy-2-ketoglutaric acid was determined to be 150 mM and D-form was not detected.

The above supernatant (50 ml) was passed through a column filled with Diaion PA 416 (Mitsubishi Kasei Corp.), followed by elution by an exponential gradient of 0–6M formic acid. Fractions containing 4-hydroxy-2-ketoglutaric acid which was eluted with 6–8 column volumes eluent were combined and concentrated under reduced pressure. Afterward, the concentrate was provided with 0.01M $Ca(OH)_2$ and adjusted to pH 7.5 therewith. To the resulting solution was added acetone to precipitate calcium salt of L-4-hydroxy-2ketoglutaric acid. Thus, 0.7 g of calcium salt of L-4-hydroxy-2-ketoglutaric acid was obtained.

EXAMPLE 6

This example was carried out in the same manner as Example 1 except that Bacillus sp. OC187 strain was used instead of *Cellvibrio gilvus* ATCC 13127 strain. The results are shown in Table 8 (see Example 7).

EXAMPLE 7

Bacillus sp. OC187 strain was cultured in L medium for 6 hours at 30° C. and the cells were collected. After washing with 0.05M Tris-maleate buffer (pH6.0), the cells were suspended in the same buffer at about $1\times10^9$ cells/ml. To this suspension was added NTG to the final concentration of 600 mg/l and the suspension was maintained at 30° C. for 20 minutes to mutagenize the cells. The mutagenized cells were smeared on MG agar medium having the composition shown in Table 7.

TABLE 7

| Composition of MG agar medium (amounts per liter) | |
|---|---|
| $KH_2PO_4$ | 2 g |
| $(NH_4)_2SO_4$ | 2 g |
| $FeSO_4.7H_2O$ | 5 mg |
| $MnSO_4.7H_2O$ | 2 mg |
| $MgSO_4.7H_2O$ | 0.5 g |
| $CaCl_2$ | 10 mg |
| Yeast extract | 1 g |
| Peptone | 1 g |
| Calcium D-galactonate | 5 g |
| Agar | 20 g |
| pH | 7.0 |

The colonies formed were transferred onto L agar medium (L medium supplemented with 2% of agar), and evaluation of the strains for their productivity of 4-hydroxy-2-ketoglutaric acid was carried out by using the same procedures as those described in Example 1 without the heat treatment. Analysis of 4-hydroxy-2-ketoglutaric acid contained in the supernatant after centrifugation, which was conducted in the same manner as in Example 1, showed the presence of a mutant, S 16, which produces only D-4-hydroxy-2-ketoglutaric acid without L-4-hydroxy-2-ketoglutaric acid. The analytical result of reaction supernatant for S 16 is shown in Table 8.

TABLE 8

| Strains | Heat treatment | Yield of 4-hydroxy-2-ketoglutaric acid (mM) | |
|---|---|---|---|
| | | D-form | L-form |
| OC 187 | not done | 28.8 | 7.7 |
| OC 187 | done | 27.6 | 0.0 |
| S 16 | not done | 27.8 | 0.0 |

What is claimed is:

1. A process for specifically producing either the R or S form of an optically active (R) or (S) 4-hydroxy-2-ketoglutaric acid which comprises:

(a) adding pyruvic acid and glyoxylic acid to a medium containing a biocatalyst selected from the group consisting of cells, a culture, and processed cells of a microorganism selected from the group consisting of *Pseudomonas putida*, *Pseudomonas saccharophila*, *Pseudomonas boreopolis*, *Pseudomonas taetrolens*, *Pseudomonas oleovorans*, *Paracoccus denitrificans*, *Providencia rustigianii*, *Rhizobium meliloti*, and *Morganella morganii*, to form an optically active 4-hydroxy-2-ketoglutaric acid; and (b) recovering said optically active 4-hydroxy-2-ketoglutaric acid.

2. A process for specifically producing either the R or S form of an optically active (R) or (S) 4-hydroxy-2-ketoglutaric acid which comprises:

(a) adding pyruvic acid and glyoxylic acid to a medium containing a biocatalyst selected from the group consisting of cells, a culture, and processed cells of a microorganism selected from the group consisting of *Pseudomonas putida* ATCC 795, *Pseudomonas putida* ATCC 4359, *Pseudomonas saccharophila* ATCC 15946, *Pseudomonas boreopolis* ATCC 15452, Pseudomonas taetrolens ATCC 17466, Pseudomonas oleovorans ATCC 8062, Paracoccus denitrificans ATCC 19367, Providencia rustigianii ATCC 13159, Rhizobium meliloti PCR 2001, Morganella Morganii ATCC 25830, Ceilvibrio gilvus ATCC 13127, Bacillus sp. OC 187, and Bacillus sp. S 16, to form an optically active 4-hydroxy-2-ketoglutaric acid; and (b) recovering said optically active 4-hydroxy-2-ketoglutaric acid.

* * * * *